(12) United States Patent
Tillman et al.

(10) Patent No.: US 11,051,733 B2
(45) Date of Patent: Jul. 6, 2021

(54) ISOLATING AND PURIFYING CELLS FOR THERAPY

(75) Inventors: Bryan Tillman, Lewisville, NC (US); Anthony Atala, Winston Salem, NC (US); James Yoo, Winston Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 12/356,982

(22) Filed: Jan. 21, 2009

(65) Prior Publication Data

US 2009/0186065 A1    Jul. 23, 2009

Related U.S. Application Data

(60) Provisional application No. 61/022,028, filed on Jan. 18, 2008.

(51) Int. Cl.

| | |
|---|---|
| *A61K 39/395* | (2006.01) |
| *A61F 2/00* | (2006.01) |
| *A61K 35/12* | (2015.01) |
| *A61B 5/153* | (2006.01) |
| *A61M 1/36* | (2006.01) |
| *C12N 5/071* | (2010.01) |
| *A61B 5/00* | (2006.01) |
| *A61B 5/15* | (2006.01) |
| *A61K 35/44* | (2015.01) |

(52) U.S. Cl.
CPC .......... *A61B 5/153* (2013.01); *A61B 5/15003* (2013.01); *A61B 5/150236* (2013.01); *A61B 5/150244* (2013.01); *A61B 5/150389* (2013.01); *A61B 5/150503* (2013.01); *A61B 5/150755* (2013.01); *A61B 5/411* (2013.01); *A61M 1/3679* (2013.01); *C12N 5/069* (2013.01); *A61B 5/416* (2013.01); *A61F 2/00* (2013.01); *A61F 2310/00371* (2013.01); *A61K 35/12* (2013.01); *A61K 35/44* (2013.01); *A61K 39/395* (2013.01)

(58) Field of Classification Search
CPC ...... A61K 39/395; A61K 35/12; A61K 35/44; A61F 2/00; A61F 2310/00371
USPC ...................................... 424/130.1, 423, 572
See application file for complete search history.

(56) References Cited

U.S. PATENT DOCUMENTS

| | | | |
|---|---|---|---|
| 1,995,970 | A | 3/1935 | Dorough |
| 2,676,945 | A | 4/1954 | Higgins |
| 2,683,136 | A | 7/1954 | Higgins |
| 2,703,316 | A | 3/1955 | Schneider |
| 2,758,987 | A | 8/1956 | Salzberg |
| 2,951,828 | A | 9/1960 | Zelle et al. |
| 3,531,561 | A | 9/1970 | Trehu |
| 4,251,387 | A | 2/1981 | Lim et al. |
| 5,266,480 | A | 11/1993 | Naughton et al. |
| 5,514,378 | A | 5/1996 | Mikos et al. |
| 5,654,273 | A | 8/1997 | Gallo et al. |
| 5,709,854 | A | 1/1998 | Griffith-Cima et al. |
| 5,738,876 | A | 4/1998 | Enevold |
| 5,785,964 | A | 7/1998 | Naughton et al. |
| 5,851,833 | A | 12/1998 | Atala |
| 5,855,610 | A | 1/1999 | Vacanti et al. |
| 5,858,721 | A | 1/1999 | Naughton et al. |
| 5,891,477 | A | 4/1999 | Lanza et al. |
| 6,140,039 | A | 10/2000 | Naughton et al. |
| 6,165,487 | A | 12/2000 | Ashkar et al. |
| 6,171,344 | B1 | 1/2001 | Atala |
| 6,376,244 | B1 | 4/2002 | Atala |
| 6,383,478 | B1 | 5/2002 | Prokop et al. |
| 6,428,802 | B1 | 8/2002 | Atala |
| 6,432,081 | B1 | 8/2002 | Atala |

(Continued)

FOREIGN PATENT DOCUMENTS

| | | |
|---|---|---|
| WO | 9819712 A1 | 5/1998 |
| WO | 0186893 A2 | 11/2001 |
| WO | 02073187 A1 | 9/2002 |

OTHER PUBLICATIONS

Michaud et al., "Circulating Endothelial Progenitor Cells From Healthy Smokers Exhibit Impaired Functional Activities", Atherosclerosis, vol. 187, pp. 423-432, 2006.

(Continued)

*Primary Examiner* — Shin Lin Chen

(74) *Attorney, Agent, or Firm* — Nelson Mullins Riley & Scarborough LLP; Thomas J. Engellenner; Reza Mollaaghababa

(57) ABSTRACT

The present invention provides methods and devices for isolating cells from a subject by circulating the subject's body fluid over an affinity moeity coupled matrix to isolate cells from a subject either ex vivo or in vivo. One aspect of the invention is directed to connecting a subject to a system capable of circulating the subject's body fluid through an affinity moiety coupled matrix, such that the affinity moiety coupled matrix is capable of binding to and extracting target cells from the body fluid, and then eluting the target cells from the affinity moiety. Another aspect of the invention is directed to the apparatus for isolating cells from a subject, comprising a blood circulation system with an arterial side blood circuit for extracting blood and flowing the blood over an affinity moiety coupled matrix that binds to and extracts target cells and a venous side blood circuit for returning the blood to the patient. The invention is also directed to in vivo seeding of biomatrials by implanting the affinity moiety coupled matrix in a subject to attract and bind the target cells in vivo.

15 Claims, 6 Drawing Sheets

(56) References Cited

U.S. PATENT DOCUMENTS

| | | | |
|---|---|---|---|
| 6,479,064 | B1 | 11/2002 | Atala |
| 6,482,645 | B2 | 11/2002 | Atala |
| 6,519,492 | B1 | 2/2003 | Yoo et al. |
| 6,569,428 | B1 | 5/2003 | Isner et al. |
| 6,576,019 | B1 | 6/2003 | Atala |
| 6,620,203 | B2 | 9/2003 | Atala |
| 6,673,339 | B1 | 1/2004 | Atala et al. |
| 6,692,738 | B2 | 2/2004 | MacLaughlin et al. |
| 6,753,181 | B2 | 6/2004 | Atala |
| 6,927,221 | B2 | 8/2005 | Hibi et al. |
| 2003/0007954 | A1 | 1/2003 | Naughton et al. |
| 2003/0068664 | A1* | 4/2003 | Albitar et al. |
| 2003/0119714 | A1 | 6/2003 | Naylor et al. |
| 2004/0161412 | A1 | 8/2004 | Penn et al. |
| 2005/0050228 | A1 | 3/2005 | Perham et al. |
| 2005/0239155 | A1* | 10/2005 | Alarcon et al. |
| 2006/0149392 | A1* | 7/2006 | Hsieh et al. |
| 2006/0240432 | A1* | 10/2006 | Ono et al. |
| 2007/0042341 | A1* | 2/2007 | Xu et al. |
| 2007/0141107 | A1* | 6/2007 | Kutryk et al. |
| 2007/0160681 | A1* | 7/2007 | Park et al. |
| 2007/0264306 | A1* | 11/2007 | Flameng et al. |
| 2008/0233087 | A1* | 9/2008 | Shamblott et al. |

OTHER PUBLICATIONS

Freshney, Culture of Animal Cells. A Manual of Basic Techniques, 2d Ed., A. R. Liss, Inc., New York, 1987, Ch. 9, pp. 107B126, Ch. 11 and 12, pp. 137B168.
Geoddel: Gene Expression Technology: Methods in Enzymology 185, Academic Press, San Diego, CA (1990).
Sambrook et al. Molecular Cloning: A Laboratory Manual, 2nd Edition, Cols Spring Harbor Laboratory press (1989).
McCutcheon's, Emulsifiers and Detergents, 1986, North American and International Editions, McCutcheon MC Publishing Co., Glen Rock, N.J., U.S.A.
Judith Neugebauer, A Guide to the Properties and Uses of Detergents in Biology and Biochemistry, Calbiochem, Hoechst Celanese Corp., 1987.
Rinsch, Gene Ther. 8, 2001, pp. 523-533.
Meana, Burns, 24, 1998, pp. 621-630.
Lu, Circulation, 104, 2001, pp. 594-599.
Penn, U.S. Appl. No. 60/405,274.
Askari, U.S. Appl. No. 60/424,065.
Cima, J Biomech Eng, 113, 1991, pp. 143-151.
Lanza, Nat Biotech, 20, 2002, pp. 689-696.
Schuch, Blood, 100, 2002, pp. 4622-4628.
Lazarous, Cardio Res, 44, 1999, pp. 294-302.
ATCC Catalog, www.atc.org/SearchCatalogs/longview.cfm?view=ce, 6466490, TIB-192&text=M1&max=20.
Lee, Circulation, 102, 2000, pp. 898-901.
Yia, Lancet, 355, 2000, pp. 213-222.
Springer, Mol Cell, 2, 1998, pp. 549-558.
Springer, J Gene Med, 2, 2000, pp. 279-288.
Bivalacqua, Am J Physiol Heart Circul Physiol, 292, 2006, pp. 1278-1290.
Gehling et al., "Partial Hepatectomy Induces Mobilization of a Unique Population of Haematopoietic Progenitor Cells in Human Healthy Liver Donors", Journal of Hepatology, vol. 43, pp. 845-853, 2005.
Hill et al., "Circulating Endothelial Progenitor Cells, Vascular Function, and Cardiovascular Risk", N Engl J Med, vol. 348, pp. 593-600, 2003.
Ingram et al., "Identification of a Novel Hierarchy of Endothelial Progenitor Cells Using Human Peripheral and Umbilical Cord Blood", Blood, vol. 104, pp. 2752-2760, 2004.
Kaushal et al., "Functional Small-Diameter Neovessels Created Using Endothelial Progenitor Cells Expanded Ex Vivo", Nature Medicine, vol. 7, pp. 1035-1040, 2001.
Kirker-Head et al., "Recombinant Bone Morphogenetic Proteins: Novel Substances for Enhancing Bone Healing", Veterinary Surgery, vol. 24, pp. 408-419, 1995.
Korbling et al., "Recombinant Human Granulocyte-Colony-Stimulating Factor-Mobilized and Apheresis-Collected Endothelial Progenitor Cells: A Novel Blood Cell Component for Therapeutic Vasculogenesis", Transfusion, vol. 46, pp. 1795-1802, 2006.
L'Heureux et al., "Human Tissue-Engineered Blood Vessels for Adult Arterial Revascularization", Nature Medicine, vol. 12, pp. 361-365, 2006.
Michaud et al., "Circulating Endothelial Progenitor Cells From Healthy Smokers Exhibit Impaired Functional Activities", vol. 187, pp. 423-432, 2006.
Michon et al., "Complications of Apheresis in Children", Transfusion, vol. 47, pp. 1837-1842, 2007.
Niklason et al., "Advances in Tissue Engineering of Blood Vessels and Other Tissues", Transplant Immunology, vol. 5, pp. 303-306, 1997.
Niklason et al., "Functional Arteries Grown in Vitro", Science, vol. 284, p. 489, 1999.
Powell et al., "Granulocyte Colony-Stimulating Factor Mobilizes Functional Endothelial Progenitor Cells in Patients With Coronary Artery Disease", Arterioscler. Thromb. Vasc. Biol., vol. 25, pp. 296-301, 2005.
Tondreau et al., "Mesenchymal Stem Cells Derived From CD133-Positive Cells in Mobilized Peripheral Blood and Cord Blood: Proliferation, Oct4 Expression, and Plasticity", Stem Cells, vol. 23, pp. 1105-1112, 2005.
Winters, "Complications of Donor Apheresis", Journal of Clinical Apheresis, vol. 21, pp. 132-141, 2006.
Yin et al., "AC133, A Novel Marker for Human Hematopoietic Stem and Progenitor Cells", Blood, vol. 90, pp. 5002-5012, 1997.

\* cited by examiner

ISOLATING AND PURIFYING CELLS FOR THERAPY

CROSS REFERENCE TO RELATED APPLICATIONS

The present application claims the benefit of U.S. Provisional Application No. 61/022,028 filed on Jan. 18, 2008, entitled "Methods of Isolating and Purifying Cells for Therapy." The entire contents of the provisional application are hereby incorporated herein by reference.

FIELD OF THE INVENTION

The present invention concerns methods of isolating cells for cell therapy and other applications. In particular, methods of isolation and purification of stem cells are disclosed.

BACKGROUND OF THE INVENTION

Use of stem cells for cell therapy and other applications is attractive due to the ability of stem cells to transform into various cell types if guided appropriately. However, one of the persisting limitations of using stem cells for applications is the limited number of cells present within the body system, which makes their utilization a challenge clinically. The current state of stem or progenitor cell procurement within the circulating system involves obtaining large volumes of blood for cell isolation. This method permits the collection of a small number of target cells per volume of blood and results in the waste of blood.

SUMMARY OF THE INVENTION

The invention is directed, in part, to selecting a target cell population using at least one cell-specific affinity moiety while retaining a subject's body fluid. The affinity moiety used to attract a desired cell population, can include, for example, antibodies, protein ligands, nucleic acids or peptides. In a preferred embodiment, the cell-specific affinity moiety includes cell-specific antibodies. In some embodiments, stem cells can be isolated using the methods of the invention. For example, the affinity moiety can be selected to have substantial affinity for a specific cell surface receptor, such as CD133, hematopoietic stem cell markers CD34, sca-1, c-kit, and CD33. This enables collection and purification of peripheral stem cells necessary for expansion and application to engineered tissues. In other embodiments, other target cells can be isolated, such as non-stem cells, diseased cells and infectious agents or toxins.

In one aspect, the invention provides a method for the collection of a large number of stem or progenitor cells and prevents unnecessary fluid loss, by returning the fluid back to the patient. The body fluid can include, but is not limited to, peripheral blood, cord blood, spinal fluid, bone marrow, amniotic fluid, cerebrospinal fluid (CSF), follicular fluid, interstitial fluid, intracellular fluid, prostatic fluid, Scarpa's fluid, seminal fluid, and synovial fluid. The methods of the present invention can be used as a safe way to isolate stem cells for banking of isolated stem cells.

This invention discloses a unique filtering method to isolate and purify specific stem or progenitor cells dispersed throughout the circulatory system. In some embodiments, the invention is based, in part, on a filtering system that is similar to dialysis or apheresis where blood cycles through a treatment device. Instead of solute transfer or nonspecific removal of cells, however, a specific cell type is extracted. All filtered blood is then returned to the patient. Once the purification is complete, the cells can be eluted from the solid state affinity matrix. The cartridge itself can be based on antibody covalently linked to a solid state matrix.

This invention can be used, for example, to purify stem cells directly from peripheral blood that is then returned to the subject immediately after being filtered. This invention enables purification of relatively rare stem cells not just from an isolated tissue specimen but from the entire pool of stem cells in a subject without depleting other cell types. By returning filtered blood to the patient other important cell types are not lost in the process. Further, the vastly increased yields of stem cells from the entire blood volume of the patient increases the cell biomass available for cell expansion for future engraftment in the patient for any of the cell types to which it is a precursor.

In yet another aspect, the invention discloses methods and systems for percutaneous extracorporeal cell isolation. Percutaneous venous vascular access avoids the need for a surgical procedure and enables blood to cycle over an affinity matrix (as beads or other flow compatible biomatrix) with the use of an external pump to a column or alternately, to a syringe based modification (e.g., matrix confined to the syringe). The latter approach enables blood to pass over the biomatrix with only small volumes extracted from the body at any time and then returned to the patient before the next volume of blood is pulled into the system.

In another aspect, the invention provides direct mobilization and adherence of selected cells to target materials, such as biomaterials, culture plates, etc. In contrast to other methods of stem cell purification, the present method does not remove blood specimens permanently from the donor and are not processed in vitro. Other methods discard cells not within the target population, whereas the present method returns the non-target population cells back to the patient.

In another aspect, an implanted vascular stent or biomaterial based vessel or organ construct coated with one or more cell specific affinity moiety can be used to filter cells, attracting stem cells to that scaffold. The cells can then colonize and ultimately recapitulate the entirety of the vessel or organ. The affinity moiety used to attract a desired cell population, can include, for example, antibodies, protein ligands, nucleic acids or peptides.

In another aspect, the invention provides a method to promote in vivo endothelialization of cardiac and vascular stents and/or prosthetics. Instead of an external cartridge, the stent itself becomes the cartridge attracting stem cells to the stent to facilitate coverage of the stent surface. Stent occlusion is a major public health issue that could be prevented by adequate cell coverage of the stent.

In another aspect, the invention provides a self-seeding scaffold for in vivo seeding of target cells comprising a biomatrix covalently coupled to an affinity moiety with substantial specificity for binding to a target cell population, wherein the affinity moiety is capable of attaching and binding to said target cells. The biomatrix can be, for example, a synthetic matrix or a decellularized matrix. The biomatrix can be a stent, or more generally, any prosthetic structure. In some embodiments, the biomatrix is covalently coupled to the affinity moiety using a linker. The invention also provides a method of in vivo biomaterial seeding. For example, one or more affinity moieties directed to a target cell type (e.g. stem cells) can be covalently attached (such as by the crosslinking agent SPDP (N-succinimidyi-3-(2-pyridyldithio)propionate, 1-Ethyl-3-[3-dimethylaminopropyl]carbodiimide hydrochloride (EDC or EDAC), N-hydroxysulfosuccinimide (Sulfo-NHS), or N-hydroxysuccinimide (NHS)) to a biomatrix to attract the target cells to vessels/organs in vivo. This feature would attract the target cells to the biomatrix, precluding the need for in-vitro culture of these cells and allow their development in a more conducive in vivo environment. In preferred embodiments, NHS is used for the covalent crosslinking to the beads, whereas EDC and SPDP is used for the scaffold covalent bonding of antibody to the graft.

In another embodiment to the invention, a self-seeding scaffold can comprise a biomatrix and a recombinant protein comprising an affinity moiety. The recombinant protein can be a single chain antibody, protein, or peptide genetically engineered to also comprise a biomatrix polymer molecule, such as collagen, for instance, to create a chimeric protein. The recombinant protein and/or chimeric protein can also be woven or incorporated into the biomatrix and can be exposed from the biomatrix to display the affinity moiety capable of attracting and binding the target cells.

In another aspect, the invention provides a method of bone marrow transplantation. Bone marrow cells can be mobilized from the bone marrow into circulation. Purification of hematopoetic precursors using the method of the invention can facilitate replacement of specific leukocyte populations. CD133 expressing precursors, in particular, are recognized for their ability to reconstitute the hematopoetic system.

In yet another aspect, the invention provides a method of cancer cell depletion. A cartridge with affinity for a non-stem cell receptor, or cells expressing specific receptors (i.e., cancer cell markers such as CD33), can be used to filter and remove the target cells from the blood, for instance, leukemia and other blood borne metastases. This approach can be used to detect cancer cells in micrometastases. This can also impart a palliative effect and/or prolong life by removing the cancer cells from circulation.

The isolation method of the present invention has many advantages over currently available techniques. Large numbers of stem or progenitor cells can be collected using the methods of the present invention. The present invention preserves all blood cells, less the target cells, and the blood cells can be returned to the circulatory system. The target cells can be moved to target locations (i.e., biomaterials, slides, culture plates, etc.) and can promote adherence using antibody systems.

In some embodiments, the invention provides a method of purifying CD133 cells from blood in continuity with the vascular circuit of a living organism.

To demonstrate the principle of this invention, CD133 antibody was used to isolate stem or progenitor cells from peripheral blood. CD133 is a recognized marker of cells that are capable of reconstituting not only endothelial, neural and smooth muscle populations, but also virtually the entire hematopoietic system. In addition CD133 expression marks several types of cancer stem cells. The Examples demonstrate that high number of purified CD133 positive cells can be isolated directly from peripheral blood using a prototype column in a circuit configuration. The system setup (shown in FIGS. 1A & B) is similar to that used in the Examples with NHS linked Sepharose beads. These beads are easily retained by a size exclusion filter on the ends of the column.

DETAILED DESCRIPTION

Figure 1A:
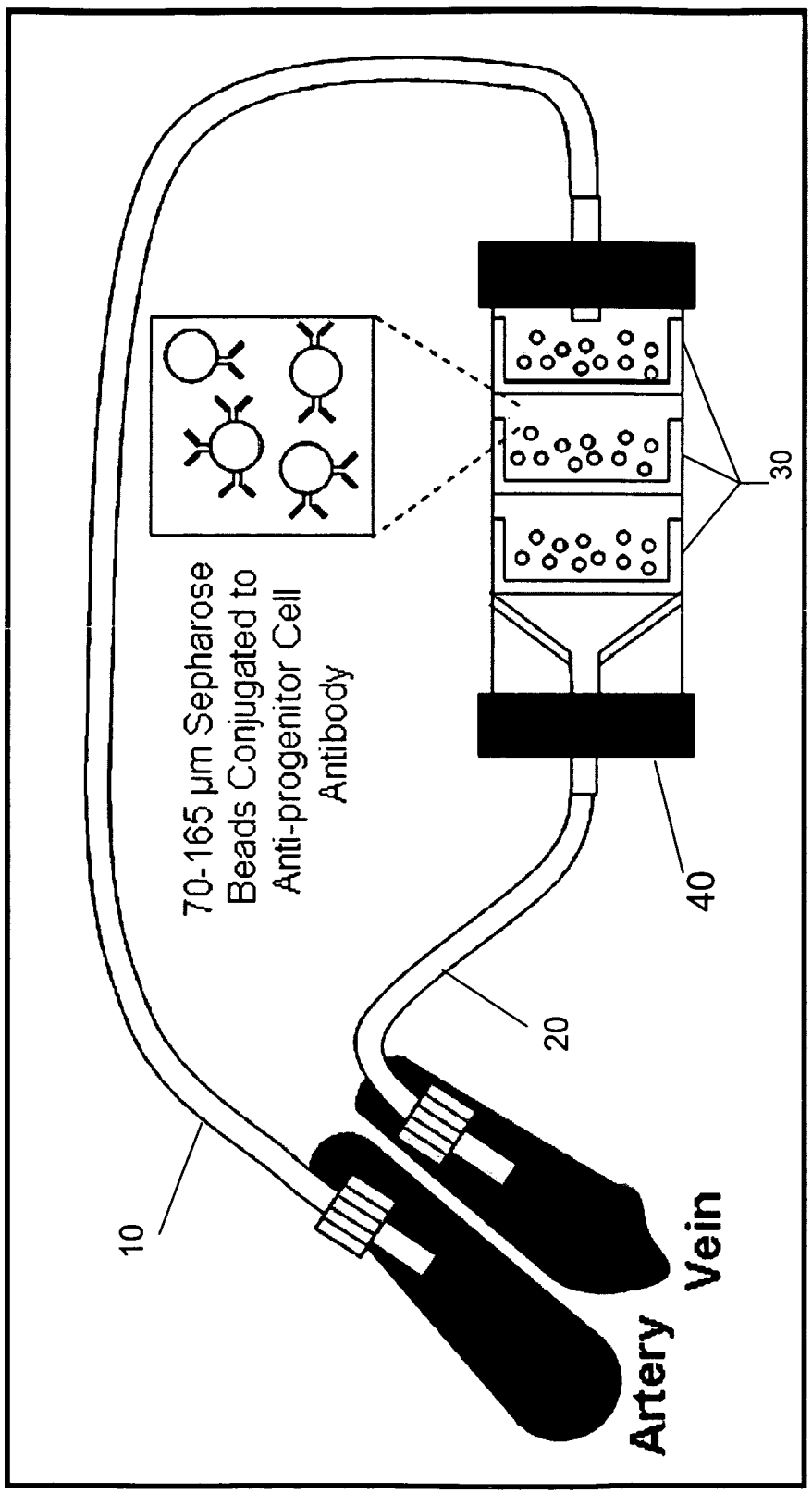
FIG. 1A is a schematic of extracorporeal cell affinity (ECA) column, 40, showing an arterial cannula, 10, carrying peripheral blood to the column, which contains three tiers of mesh filters, 30, retaining antibody-coated sepharose beads (70-165 µm diameter, inset), where CD133+ cells are retained while unbound cells and plasma are returned to the donor by a venous cannula, 20.
Figure 1B:
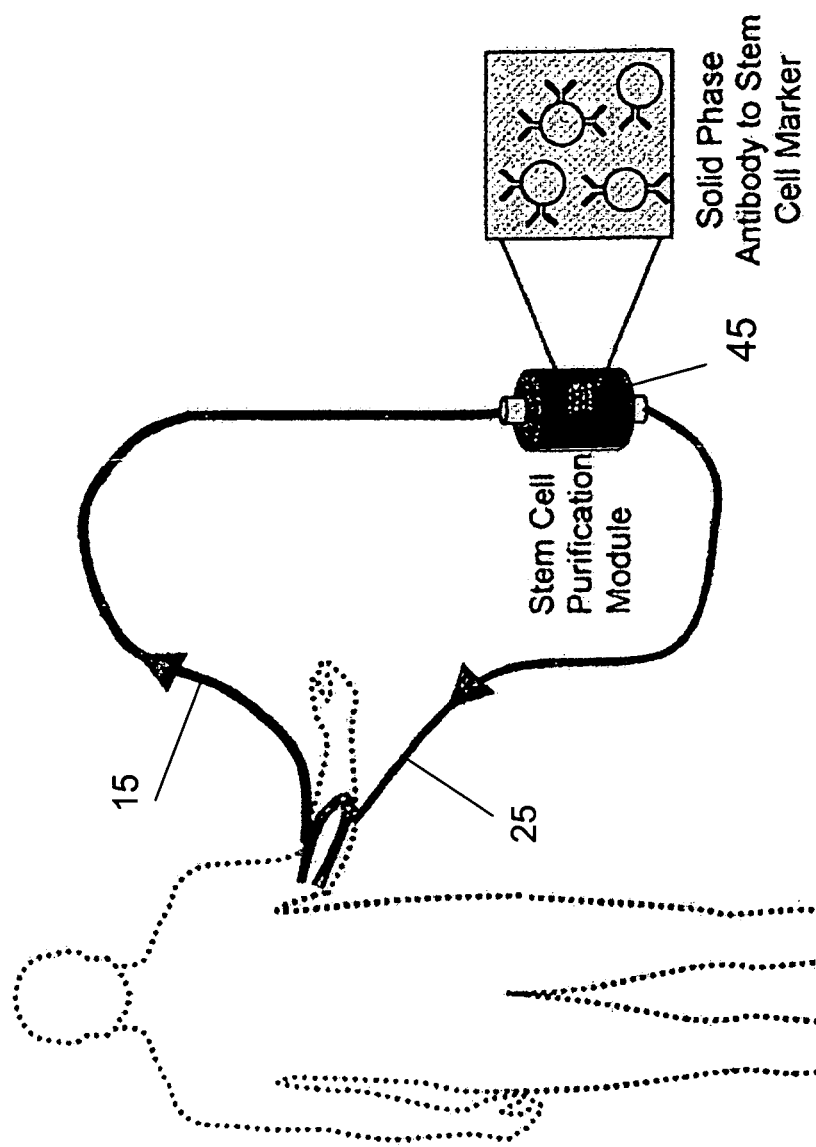
FIG. 1B is a schematic of affinity isolation of peripheral blood stem cells; Antibody affixed to a matrix binds to cells dependent on the antibody affinity from the incoming blood from the patient, 15. The matrix bound cells are confined to the cartridge, 45, by a size exclusion filter that allows blood, but not the matrix or attached cells to pass. Effluent blood, 25, is returned to the patient. The cells are later eluted from the matrix.

The terms used in this invention adhere to standard definitions generally accepted by those having ordinary skill in the art. In case any further explanation might be needed, certain terms have been further elucidated below.

The term "attach" or "attaches" as used herein refers to cells that adhere directly or indirectly to a substrate as well as to cells that adhere to other cells.

The terms "biocompatible substrate" and "biomaterial" as used herein refer to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of an structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

The term "subject" refers to any living organism in which an immune response is elicited. The term refers to a living animal or human in need of treatment for, or susceptible to, a condition involving an unwanted or undesirable microorganism, e.g., a particular treatment for having an unwanted pathogenic cell as defined below. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

As used herein, the terms "embryonic stem cell" refers to a stem cell that is derived from the inner cell mass of a blastocyst (e.g., a 4- to 7-day-old human embryo) and that is pluripotent. The term "embryonic-like stem cell" is used herein to refer to a stem cell that is not derived from the inner cell mass of a blastocyst. An embryonic-like stem cell is pluripotent. The embryonic-like stem cells display at least a subset of characteristics of embryonic stem cells (ES) and hematopoietic stem cells.

As used herein, the term "pluripotential", "pluripotential for differentiation" or "pluripotent" refers that the cell is positive for one or more of the pluripotent markers such as but are not limited to Oct-4, Nanog, and Sox-2 and the cell has the potential to differentiate to at least a subset of the mammalian body's approximately 260 cell types upon appropriate stimulations such as by the appropriate growth factors.

As used herein, the term "totipotent cell" refers to a cell that is able to form a complete embryo (e.g., a blastocyst).

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted. Non-limiting examples of stem cell markers include, for example, CD133, CD34, sca-1 and c-kit. The term "stem cell" is intended to include, for example, hematopoietic stem cells, embryonic stem cells, embryonic-like stem cells, mesenchymal stem cells, myeloid stem cell, neuronal stem cells, and adult stem cells.

The term "undifferentiated" as used herein refers to pluripotent embryonic stem cells which have not developed a characteristic of a more specialized cell. As will be recognized by one of skill in the art, the terms "undifferentiated" and "differentiated" are relative with respect to each other. A cell which is "differentiated" has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known markers of differentiation. A marker of differentiation indicating that cells are differentiated or undifferentiated includes a protein, carbohydrate, lipid, nucleic acid, functional characteristic and/or morphological characteristic which is specific to a differentiated cell.

As used herein, the term "substantially homogeneous" when applied to cells, refers to a population of cells, wherein at least about 70%, and preferably about 80%, more preferably 90% of the cells in the population are of the same cell type. Examples of cell types include, but are not limited to, embryonic-like stem cells, beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, retinal cells, and the like. In some embodiments, the term "substantially homogeneous" describes a population of cells wherein at least about 70%, and preferably about 80%, more preferably 90% of the cells in the population are undifferentiated. In a further embodiment a substantially homogeneous population of cells is one in which more than 95% of the cells are undifferentiated. In another embodiment, a substantially homogeneous population of cells is one in which more than 99% of the cells are undifferentiated. A population of cells can be assayed for one or more markers of differentiation to determine whether the population of cells is substantially homogeneous.

The phrases "augmenting organ function" or "augmenting function of an organ" as used herein refers to increasing, enhancing, improving, the function of an organ that is operating at less than optimum capacity. The term is used to refer to a gain in function so that the organ is operating at a physiologically acceptable capacity for that subject. For example, the physiological acceptable capacity for an organ from a child, e.g., a kidney or heart, would be different from the physiological acceptable capacity of an adult, or an elderly patient. The entire organ, or part of the organ can be augmented. Preferably the augmentation results in an organ with the same physiological response as a native organ. In a preferred embodiment, an organ is augmented in capacity when it is functioning to at least at 10% of its natural capacity.

The phrases "three-dimensional biomatrix" or "augmenting construct" or "neomorphic organ augmenting structure" as used herein refers to a mini-matrix that has been perfused with the cells and cultured until the cells form a tissue layer. The tissue layer can be a single monolayer, or multiple layers. Tissue-specific cells refer to cells derived from the specific organ requiring augmentation, e.g., cells from a kidney organ for organ augmentation, and cells from a heart for heart organ augmentation. The cells in the three-dimensional biomatrix establish a "tissue-like" histology, can regenerate tissue-like architecture, and develop into primitive organoids with complex, multilayered structures that can eventually develop into the actual organ, or part of the organ. The three-dimensional biomatrix is an artificial organ, or part of an organ that is the "functional equivalent" of the natural organ, i.e., behaves in the same, or similar manner as a natural organ, for example, the artificial kidney has the same functional characteristics as an in vivo kidney. For example, a kidney augmenting structure can be one that has a layer of tissue capable of developing into nephron structures, or part of a nephron structure. For kidney augmentation, the tissue specific cells can be an isolated population of cells selected from the group consisting of distil tubule cells, proximal tubule cells glomeruli cells, Bowman's capsule cells, and loop of Henlé cells. Alternatively, the tissue specific cells can be a mixed population of cells that includes distil tubule cells, proximal tubule cells, glomeruli cells, Bowman's capsule cells, and loop of Henlé cells. Various three-dimensional biomatrices that address specific diseases or disorders can be created. For example, the three-dimensional biomatrix can be specifically created to ameliorate disorders associated with the glomerulus by using a homogenous population of glomeruli cells that are used to perfuse the matrix material. Alternatively, the three-dimensional biomatrix can be a general construct created using a mixed population of renal cells. When the three-dimensional biomatrix is brought into contact with a host tissue at a target site in the organ, it is able to grow and proliferate within the target site and replenish or augment the depleted activity of the organ at that site. The augmenting construct can be added at a single location in the organ. Alternatively, a plurality of augmenting constructs can be created and added to multiple sites in the organ.

As used herein, the term "linker" is intended to refer to a molecule capable of crosslinking to a specific functional group on a molecule. Non-limiting examples of linkers useful with the present invention include SPDP (N-succinimidyl-3-(2-pyridyldithio)propionate), 1-Ethyl-3-[3-dimethylaminopropyl]carbodiimide hydrochloride (EDC or EDAC), N-hydroxysulfosuccinimide (Sulfo-NHS), N-hydroxysuccinimide (NHS), N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), N-sulfosuccinimidyl-3-(2-(5-nitro-pyridyldithio) butyrate (SSNPB), 2-iminothiolane, or S-acetylsuccinic anhydride.

The term "target site" as used herein refers to a region in the organ that requires augmentation. The target site can be a single region in the organ, or can be multiple regions in the organ. The entire organ, or part of the organ can be augmented. Preferably the augmentation results in an organ with the same physiological response as a normal organ. The entire organ can be augmented by placing a plurality of biomatrices at suitable distances along the entire organ, e.g., along the entire longitudinal section of a kidney. Alternatively, part of the organ can be augmented by placing at least one biomatrix in one target site of the organ, e.g., the top of the kidney.

I. Cells

There exists a need for better methods for isolation and purification of multipotential progenitor cells from peripheral blood. In particular, new methods for isolating stem cells from the peripheral blood of a living donor while minimizing losses of other hematopoetic cell types would satisfy a long-felt therapeutic need.

The methods and apparatus of the present invention enable the use of autologous cell populations derived from the subject's own tissue to be efficiently isolated. In some other embodiments, allogenic cells derived from a different individual of the same species can be used to obtain isolated populations for use.

Methods for the culture of cells isolated using methods of the present invention are discussed by Freshney, *Culture of Animal Cells. A Manual of Basic Technique*, 2d Ed., A. R. Liss, Inc., New York, 1987, Ch. 9, pp. 107-126.

Cells can be isolated from a number of sources, for example, cells can be isolated from a subject's body fluid, such as, peripheral blood, cord blood, spinal fluid, bone marrow, amniotic fluid, cerebrospinal fluid (CSF), follicular fluid, interstitial fluid, intracellular fluid, prostatic fluid, Scarpa's fluid, seminal fluid, and synovial fluid.

Cell types include, but are not limited to, endothelial cells such as human endothelial cells, progenitor cells isolated from the peripheral blood or bone marrow that can be induced to differentiate into different cells, embryonic stem cells, embryonic-like stem cell, mesenchymal stem cells, myeloid stem cells, neuronal stem cells, adult stem cells, committed stem cells, and/or differentiated cells may be used. In a preferred embodiment, endothelial progenitor cells are autologously derived from peripheral blood.

Also, depending on the type of tissue or organ being made, specific types of committed stem cells can be used. For instance, myoblast cells can be used to build various muscle structures. Other types of committed stem cells can be used to make organs or organ-like tissue such as heart, kidney, liver, pancreas, spleen, bladder, ureter and urethra. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, endothelial cells, hormone-secreting cells, cells of the immune system, neurons, cells from the heart, kidney, liver, pancreas, spleen, bladder, ureter and urethra, and the like. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

Examples also include cells that have been genetically engineered, transformed cells, and immortalized cells. One example of genetically engineered cells useful in the present invention is a genetically engineered cell that makes and secretes one or more desired molecules. When matrices comprising genetically engineered cells are implanted in an organism, the molecules expressed can produce a local effect or a systemic effect, and can include the molecules identified above as possible substances.

Cells can produce substances that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix.

Cell fractionation can also be desirable, for example, when the donor has diseases such as cancer or tumor. A cell population can be sorted to separate the cancer or tumor cells from normal noncancerous cells. The normal noncancerous cells, isolated from one or more sorting techniques, can then be used for tissue reconstruction. Other techniques known by those skilled in the art can also be used to isolate non-diseased cells, these can include but are not limited to, selective adhesion and selective cloning. These methods and others are discussed by Bonifacino et al, *Current Protocols in Cell Biology*, John Wiley and Sons, Inc., New Jersey, 2007, which is herein incorporated by reference in its entirety.

Isolated cells can be cultured in vitro to increase the number of cells available for seeding into the biocompatible substrate. To prevent an immunological response after implantation of the artificial tissue construct, the subject may be treated with immunosuppressive agents such as, cyclosporin or FK506.

Isolated cells can be transfected with a nucleic acid sequence. Useful nucleic acid sequences can be, for example, genetic sequences which reduce or eliminate an immune response in the host. For example, the expression of cell surface antigens such as class I and class II histocompatibility antigens can be suppressed. In addition, transfection can also be used for gene delivery. Cells can be transfected with specific genes prior to seeding onto the biocompatible matrix. Thus, the cultured cells can be engineered to express gene products that produce a desired protein to help ameliorate a particular disorder. Another example of genetic engineering can be modifying the tissue cells to produce gene products beneficial to implantation, e.g., anti-inflammatory factors, e.g. anti-GM-CSF, anti-TNF, anti-IL-1, and anti-IL-2. Alternatively, the tissue cells can be genetically engineered to "knock out" expression of native gene products that promote inflammation, e.g., GM-CSF, TNF, IL-1, IL-2, or "knock out" expression of MHC in order to lower the risk of rejection.

Methods for genetically engineering cells, for example with retroviral vectors, adenoviral vectors, adeno-associated viral vectors, polyethylene glycol, or other methods known to those skilled in the art, can be used. These include using expression vectors which transport and express nucleic acid molecules in the cells. (See Geoddel; *Gene Expression Technology: Methods in Enzymology* 185, Academic Press, San Diego, Calif. (1990).

Vector DNA can be introduced into prokaryotic or eukaryotic cells via conventional transformation or transfection techniques. Suitable methods for transforming or transfecting host cells can be found in Sambrook et al. *Molecular Cloning: A Laboratory Manual,* 2nd Edition, Cold Spring Harbor Laboratory press (1989), and other laboratory textbooks.

The invention can be further described using a cell surface marker affinity technique. CD133 is a surface antigen of, as yet, unknown function that serves as a marker of multipotential progenitor cells. Cells expressing CD133 constitute the progenitors of such diverse cell types as hepatocytes, neural lineages, vascular endothelium, and smooth muscle cells. Further, they possess the ability to reconstitute the entire hematopoetic system. These attributes have led to the use of CD133 positive cells in clinical trials for a variety of applications including cardiac, hepatic, and muscle regeneration as well as in bone marrow transplantion. In addition, cells expressing CD133 have been used as the progenitors in a variety of bioengineered tissues.

CD133 positive cells are infrequent in isolated peripheral blood, ranging from about 0.01 to 0.0001% of leukocytes. In the context of endothelial differentiation, the percentage of cells capable of forming colonies is even more scarce, approximately 1 colony in 100 million leukocytes. The low numbers of circulating CD133 positive endothelial progenitor cells remains a major obstacle to clinical applications of autologous CD133 positive endothelial progenitor cells. Approaches for in vitro purification of progenitor cells from peripheral blood and marrow specimens have been described and are widely employed. Limitations persist however, in the ability of these strategies to achieve relevant numbers of cells at low passage before senescence. Towards the goal of attaining a clinically useful number of cells, current in vitro purification techniques are limited. The volume of blood that can be safely removed from a living donor is limited and this, in turn, limits the yield of prospective progenitor cells for expansion.

Other surface markers that can be used in this invention can include, but are not limited to, CD34, an adhesion marker found on multiple progenitor cell populations, such as bone marrow, umbilical cord hematopoietic cells and endothelial progenitors, sca-1, also known as stem cell antigen is found on early hematopoietic progenitor and stem cells, and c-kit, another early progenitor and stem cell marker. Isolation techniques can be based on one or more surface markers. For example, isolation of CD133 positive cells can be followed by isolation of CD34 cells or isolation of cells expressing both CD133 and CD34 can be performed simultaneously.

CD33 is a transmembrane receptor found on monocytic and myeloid lineage cells. Its expression on most acute myeloid leukemia cells make it an attractive selective agent for treatments. Antibody-based treatments targeting CD33 positive cells are currently being used for acute myeloid leukemia. In yet another aspect, the invention provides a method for cancer cell depletion, wherein the target cell is a cancer cell. A cartridge with affinity for a non-stem cell receptor, or cells expressing specific receptors (i.e., cancer cell markers, such as CD33), can be used to filter and remove the target cells from the blood, for instance, leukemia and other blood borne metastases. This approach can be used to detect cancer cells in micrometastases or can impart a palliative effect and/or prolong life.

II. Isolation Techniques

Peripheral autologous CD133 positive stem cells have been differentiated into a variety of cell types with clinical utility. However due to a significant limitation of these cells in the infrequency collected in peripheral blood specimens, new techniques are needed. To address this problem, an extracorporeal cellular affinity (ECA) column was developed that can recover progenitor cells that express CD133, for example, with high efficiency with minimal effect on hematologic and physiologic parameters. This approach can generate over 600 fold more endothelial colony forming units than buffy leukocytes from an isolated peripheral blood specimen. Furthermore, the increased cell recovery of the ECA column can enable the generation of a cell biomass suitable for therapeutic purposes in nearly a third of the time compared to buffy leukocyte derived cells. This technology can facilitate the generation of large numbers of progenitor derived cells for clinical therapies and reduce the time required to attain clinically relevant cell numbers while minimizing loss of other important cell types to the donor.

Current in vitro techniques for isolation of cells expressing CD133, or other surface markers, are limited by the finite amount of sample, such as blood, that can be collected from an autologous donor and, in turn, the number of cells for downstream expansion. In fact, patients most likely to benefit from progenitor cell therapies, such as patients with coronary artery disease, end stage renal disease and diabetes are also the least likely to tolerate large volume blood donation for in vitro processing. Thus the invention relates to a system that allows selective recovery of the progenitor cells of interest from the entire blood volume of the donor without affecting other blood cell types.

In a clinical setting, treatment with granulocyte colony stimulating factor (G-CSF) increases the numbers of circulating CD133 positive endothelial progenitor cells by a factor of 8 to 10 fold (Korbling, M., et al., *Transfusion,* 2006. 46(10): p. 1795-802; Powell, T. M., et al., *Arterioscler Thromb Vasc Biol,* 2005. 25(2): p. 296-301.). Capitalizing on this increase in progenitors still requires a means to harvest cells safely from blood. Approaches used clinically include phlebotomy and apheresis, with or without G-CSF pretreatment, but the former is limited by the volume of blood that can be safely drawn and the latter is not without complications, either (Michon, B., et al., *Transfusion,* 2007. 47(10): p. 1837-42; Winters, J. L., *J Clin Apher,* 2006. 21(2): p. 132-41). Additionally, with apheresis, non-specific removal of all leukocyte populations results in loss of these important cell types. In contrast, the ECA column described here targets specific leukocyte subsets, in this case CD133+ cells, with no decrease in other leukocyte populations and no significant decrements in hematocrit, platelet count or circulating blood volume.

Endothelial cells derived from buffy leukocyte progenitors have been described by a number of investigators for generation of engineered vascular constructs and other clinical applications (Kaushal, S., et al., *Nat Med,* 2001. 7(9): p. 1035-40; L'Heureux, N., et al., *Nat Med,* 2006. 12(3): p. 361-5; Niklason, L. E., et al., *Science,* 1999. 284(5413): p. 489-93; Niklason, L. E. and R. S. Langer, *Transpl Immunol,*

1997. 5(4): p. 303-6.). However, only a small number of progenitors from buffy coats can be recovered from blood volumes safely recovered from an individual in a single setting. Current methods require a prolonged duration of culture to expand cell numbers to those achieved by more plentiful column isolated progenitors. Unlike current methods, no deleterious effects on cell counts, such as neutropenia, anemia, or thrombocytopenia have been observed with the use of ECA columns. In fact, comparison of complete blood counts before and after ECA column use revealed only a small but statistically significant rise in neutrophil and eosinophil counts. These changes are expected given the use of a murine anti-CD133 antibody on this column. A small but significant elevation observed in hematocrit between experimental groups was similarly observed. Importantly, there were no statistically significant decrements in platelet count and no significant alteration of physiologic parameters during column use.

One embodiment of the invention relates to a method of isolating cells from a subject using an affinity moiety coupled matrix, such as an extracorporeal cell affinity (ECA) column system. The subject can be connected to the system such that the subject's body fluid circulates through the affinity coupled matrix system. As the subject's body fluid passes through the affinity coupled matrix, the affinity moiety coupled matrix can bind to and extract target cells from the body fluid. After passing through the affinity moiety coupled matrix, the body fluid can then be returned to the subject. Once a sufficient volume of the subject's body fluid has passed through the affinity moiety coupled matrix system and the target cells can be eluted from the affinity moiety.

The affinity moiety coupled matrix, such as the extracorporeal cell affinity column can also comprise beads that act as a matrix coupled to the affinity moiety. A number of systems employing beads as a matrix coupled to the affinity moiety have proven useful for cell sorting and isolation in vitro. These include a magnetic bead system using antibody coated beads to isolate CD133 cells from small leukocyte specimens. These magnetic beads may seem applicable to ex-vivo recovery as well, however, the sub-cellular bead size make it difficult to retain the beads bound to the cells in a high flow vascular circuit. In contrast, the extracorporeal cell affinity (ECA) column system described here employs large, antibody conjugated sepharose beads which are easily retained by an appropriately sized mesh strainer while allowing ready passage of unbound cells back to the donor. One of ordinary skill in the art would be familiar with other beads with similar physiological properties that can also be employed as a matrix coupled to the affinity moiety, such as but not limited to, agarose or variants of agarose beads. Replacement of the beads can be similarly achieved by substituting matrix channels crosslinked to the antibody or ligand of interest, for instance a cardiopulmonary bypass blood filter covalently crosslinked to an antibody or ligand. Additional embodiments can include coupling the affinity moiety to a biomaterial or biomatrix, such as an implantable matrix.

Another aspect of the present invention, an affinity moiety can bind directly to the target cells. The affinity moiety can be covalently bound to the matrix. The affinity moiety can also be covalently bound to the matrix via a linker. Preferably the affinity moiety is coupled to the matrix, such as through covalent bonds, crosslinking or an equivalent interaction. The affinity moiety can be selected from the group consisting of antibodies, such as those specific for CD133, protein ligands, nucleic acids, peptides and any other agents for selectively isolating the target cells that are known by those skilled in the art. The affinity moiety can also bind the target cells through an indirect interaction. Such indirect interactions can include, but are not limited to, secondary antibodies, linkers, protein ligands, nucleic acids, peptides and other methods utilized by skilled artisans.

Figure 2:
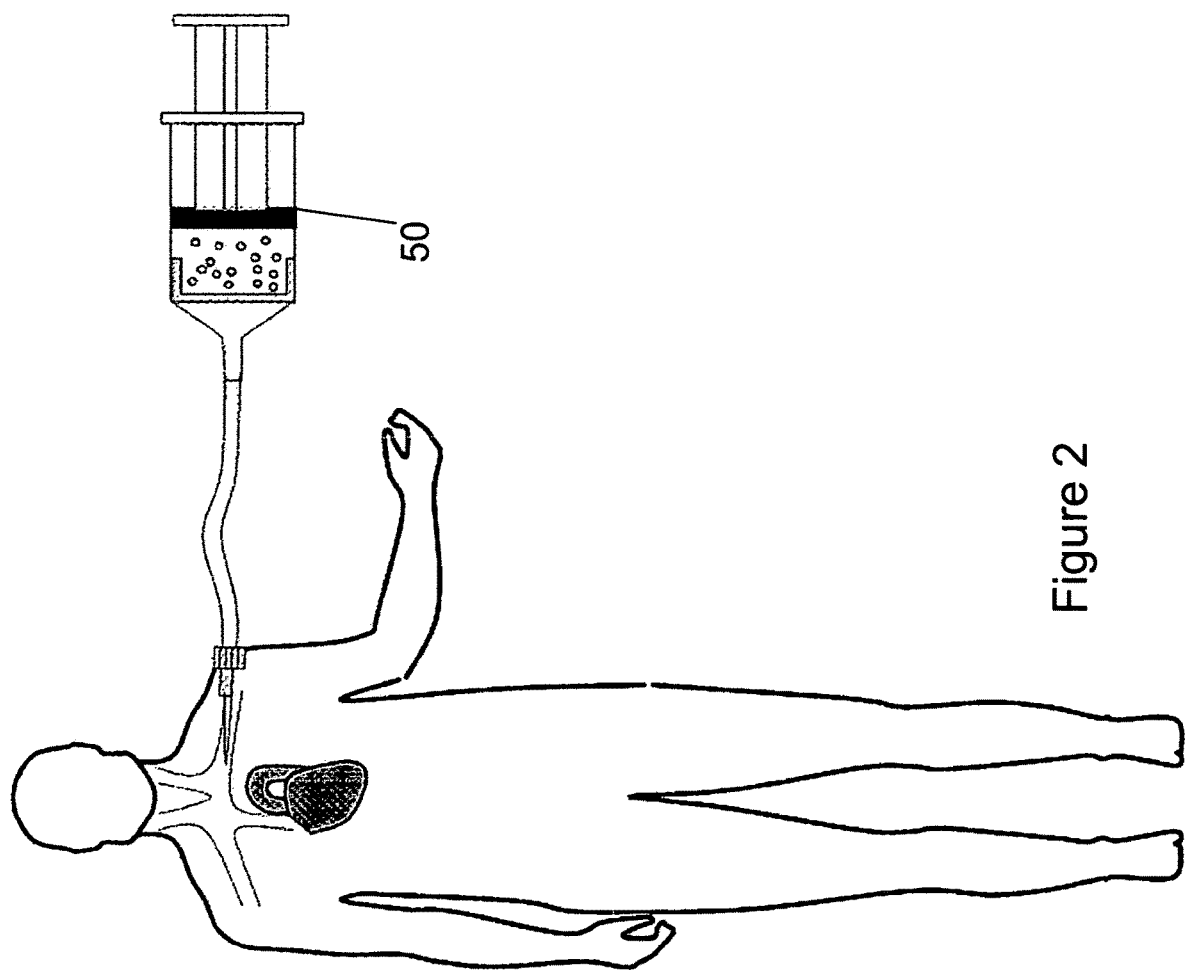
FIG. 2 is a schematic diagram of a system and apparatus for percutaneous extracorporeal cell isolation, 50.

In another aspect of the invention, the subject's body fluid is connected to the affinity coupled matrix system. Connecting the subject's body fluid to the affinity coupled matrix system can be performed surgically under the supervision of an experienced physician or one skilled in the art. For example, a surgical procedure may be required to expose and cannulate the subject's artery or vein to be connected with the affinity coupled matrix system. In some embodiments, the subject is connected to the system via an arteriovenous or veno-venous flow. The approach of an arteriovenous column system has the advantage that it is perfused passively by arterial pressure at a rate that averages 120 mL per minute. A veno-venous approach using a syringe, roller, or valve pump system can also be utilized. The veno-venous system can be applied percutaneously, (FIG. 2) similar to dialysis access, thereby avoiding surgical procedures altogether. In some other embodiments, the subject's body fluid is connected to an inlet side of the system for extracting the body fluid from the subject. The subject's body fluid can include but is not limited to peripheral blood, cord blood, spinal fluid, bone marrow, amniotic fluid, cerebrospinal fluid (CSF), follicular fluid, interstitial fluid, intracellular fluid, prostatic fluid, Scarpa's fluid, seminal fluid, and synovial fluid.

Another aspect of the invention comprises passing the subject's body fluid over the affinity moiety coupled matrix to bind to and extract target cells from the body fluid. The affinity moiety coupled matrix acts as a filtering mechanism to remove the target cells while allowing the remaining cells, particles and fluid to flow through. The flow through or remaining body fluid can be collected after passing over the affinity moiety and returned to the subject through an outlet side of the connection.

In yet another aspect of the invention, the subject's body fluid is disconnected from the affinity moiety coupled matrix system. In some embodiments where surgical intervention is required to connect the subject to the affinity moiety coupled matrix system, additional surgical procedures may be required to disconnect the subject.

Another further aspect of the invention, the target cells can be eluted from the affinity moiety. The target cells can be gently washed away from the affinity moiety with sterile saline or an equivalent buffer. In some other embodiments, the target cells are detached from the affinity moiety through a shift in pH, buffer/salt concentration, temperature, enzymatic action, or other means dependent on the affinity moiety and known by those familiar in the art.

To date, in vitro culturing has been a necessary step to expand stem cells as they differentiate towards a target population. Another benefit to ECA column isolation of target cells is increasing cell yield. Obtaining larger quantities of target cells leads to reduced culture duration to increase cell number. The risks associated with cell culturing, such as cell senescence and culture related infection prior to implantation, would also be reduced. The use of an affinity moiety coupled based system significantly minimizes culture time to attain a desired biomass of progenitor derived cells. Specifically, 0.72 colonies were generated from 10 milliliters of peripheral ovine blood isolated from an ECA column as compared to published data for human colony assays where one colony was isolated from a comparable 20 milliliters of blood (Ingram, D. A., et al., *Blood*, 2004. 104(9): p. 2752-60.), indicating an almost two fold increase in the number of colony forming cells obtained.

ECA column derived cells can generate a large number of colony forming units when extrapolated from our buffy leukocyte colony assay for an equivalent amount of blood. This observation can suggest that ECA derived cells are not just enriched in number but also in growth potential. Explanations for this phenomenon might include a paracrine effect from a higher density of column isolated CD133+ cells or alternately, an absence of negative regulation by contaminating cell types that would otherwise be present in buffy leukocyte populations. In support of this concept, the number of colony forming units cannot be enhanced by simply increasing the density of buffy coat leukocytes in culture, and, in fact, the appearance of colonies actually decreased substantially when buffy leukocytes were plated at higher density.

ECA column isolated CD133 positive cells are capable of differentiation into a broad range of cell types, including muscle, cartilage, nerve, hepatocyte and hematopoetic lineages (Gehling, U. M., et al., *J Hepatol*, 2005. 43(5): p. 845-53; Tondreau, T., et al., *Stem Cells*, 2005. 23(8): p. 1105-12; Yin, A. H., et al., *Blood*, 1997. 90(12): p. 5002-12.). The ECA column system also allows for substantially higher yields of CD133 progenitor cells with increased growth potential that can, in turn, reduce the time necessary to reach clinically useful numbers of endothelial cells. By reducing the duration of ex vivo culture and also the passage number, the cells implanted are less likely to become senescent prior to clinical application. Given reports of decreased absolute numbers of endothelial progenitor cells in patient populations with diabetes, renal failure, hypercholesterolemia, hypertension and smoking (Powell, T. M., et al., *Arterioscler Thromb Vasc Biol*, 2005. 25(2): p. 296-301; Hill, J. M., et al., *N Engl J Med*, 2003. 348(7): p. 593-600) Michaud, S. E., et al., *Atherosclerosis*, 2006. 187(2): p. 423-32., this technology can prove particularly useful in patients who stand to benefit most from progenitor based therapies. Finally, this system can be broadly applicable to the isolation of other cell types expressing specific cell surface markers, such as alternate peripheral progenitor markers or even non-progenitor cell types.

III. Matrices

The cells isolated using the methods and apparatus of the present invention can be seeded on artificial tissue. The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The phrase "three-dimensional scaffold" as used herein refers to the residual infra-structure formed when a natural biostructure, e.g. an organ, is decellularized. This complex, three-dimensional, scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold can be perfused with a population of cultured cells, e.g., endothelial cells, which grow and develop to provide an endothelial tissue layer capable of supporting growth and development of at least one additional cultured cell population.

The term "natural biostructure" as used herein refers to a biological arrangement found within a subject, for example, organs, that include but are not limited, heart, kidney, liver, pancreas, spleen, bladder, ureter and urethra. The term "natural biostructure" is also intended to include parts of biostructures, for example parts of organs, for example, the renal artery of a kidney.

The term "biomatrix," as used herein, refers to any materials which do not have toxic or injurious effects on biological functions. Natural or synthetic polymers can be used as the biomatrix, although synthetic polymers are preferred for reproducibility and controlled release kinetics. Synthetic polymers that can be used to form the microspheres include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide. Examples of natural polymers include proteins such as albumin, collagen, synthetic polyamino acids, and prolamines, and polysaccharides such as alginate, heparin, and other naturally occurring biodegradable polymers of sugar units.

The normally charged outer layer of the microcapsules can be covered by water soluble non-ionic polymers such as poly(ethylene oxide) (PEO) which act to shield the charge. These polymers are grafted to the polycationic polymers, such as poly-L-lysine (PLL) molecules used as at least one of the layers of the microcapsule, such that they create a non-ionic barrier between the outer layer of the microcapsule (made of essentially either polycationic polymers, such as PLL, or polyanionic polymers, such as alginate) and the target tissue.

Alginates are linear polymers of mannuronic and guluronic acid residues. Monovalent cation alginate salts, e.g., Na-alginate, are generally soluble. Divalent cations such as $Ca^{2+}$, $Ba^{2+}$ or $Sr^{2+}$ tend to interact with guluronate, providing crosslinking and forming stable alginate gels. Alginate encapsulation techniques typically take advantage of the gelling of alginate in the presence of divalent cation solutions. Alginate encapsulation of cells generally involves suspending the cells to be encapsulated in a solution of a monovalent cation alginate salt, generating droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, wherein the cell is suffused with a solution of multivalent ions (e.g., divalent cations) and then suspended in a solution of gelling polymer (e.g., alginate), to provide a coating of the polymer.

PLA, PGA and PLA/PGA copolymers are particularly useful for forming microspheres. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

A biomatrix can also be biodegradable. Biodegradable refers to material that can be absorbed or degraded in a patient's body. Representative materials for forming the biodegradable structure include natural or synthetic polymers, such as, for example, collagen, poly (alpha esters) such as poly (lactate acid), poly (glycolic acid) (PGA), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

The biomatrix can be non-biodegradable such the growth factor can be secreted through the matrix while the cells remain immunoisolated from the target tissue into which they are implanted. Semipermeable microcapsules can be produced through interfacial polymerization as described in U.S. Pat. No. 4,251,387. In a preferred embodiment, alginate-PLL capsules are used. Microencapsulation of cells generally involves three steps: (a) generating microcapsules enclosing the cells (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

Natural biostructures, e.g. a blood vessel or an organ, can be obtained from a donor of the same species as the subject, for example, a human cadaver blood vessel or organ for a human recipient. The natural biostructure can also be obtained from a different species which includes, but is not limited to, monkeys, dogs, cats, mice, rats, cows, horses, pigs, goats and sheep. The natural biostructure can also be obtained from the subject requiring a reconstructed organ and can have the dysfunctional blood vessel removed and decellularized using the process described below. The decellularized blood vessel of the subject can be used as the three-dimensional scaffold to reconstruct an artificial blood vessel using cultured endothelial cells (e.g., human endothelial cells) isolated from the subject. In one embodiment, the cells are isolated from subject using the methodsd of the invention can be seeded onto decellularized matrices.

Biostructures, e.g., blood vessels, or parts of blood vessels can be decellularized by removing the entire cellular and tissue content from the blood vessel. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components an the nuclear components.

Preferably, the biostructure is decellularized by removing the cell membrane and cellular debris surrounding the blood vessel using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the blood vessel, agitating the blood vessel, or stirring the blood vessel in a suitable volume of fluid, e.g., distilled water. In one embodiment, the gentle mechanical disruption method includes magnetically stirring (e.g., using a magnetic stir bar and a magnetic plate) the blood in a suitable volume of distilled water until the cell membrane is disrupted and the cellular debris has been removed from the blood vessel.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octyl-α-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem, Hoechst Celanese Corp., 1987. In one preferred embodiment, the non-ionic surfactant is the Triton series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

IV. Implantation of the Isolated Cells onto Matrices

The invention also pertains to generating artificial tissue constructs by seeding the isolated cells onto or into available biocompatible matrices. The cells can be seeded onto the matrices either in vitro or in vivo. Biocompatible refers to materials that do not have toxic or injurious effects on biological functions. Biodegradable refers to material that can be absorbed or degraded in a patient's body. Representative materials for forming the biodegradable material include natural or synthetic polymers, such as, collagen, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material.

Polyglycolic acid and polyglactin fibers may be used as supplied by the manufacturer. Other biodegradable materials include, but are not limited to, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the biocompatible substrate is enhanced by coating the matrix with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the matrix provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

Coating refers to coating or permeating a matrix with a material such as, liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix can be weaved, compression molded and glued together. Furthermore different polymeric materials shaped by different processes may be joined together to form a composite shape. The composite shape can be a laminar structure. For example, a polymeric matrix may be attached to one or more polymeric matrixes to form a multilayer polymeric matrix structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized for mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

The shape of the extracellular matrix may help send signals to the cells to grow and reproduce in a specific type of desired way. Other factors and differentiation inducers may be added to the matrix to promote specific types of cell growth.

Substrates can be treated with additives or drugs prior to implantation (before or after the polymeric substrate is seeded with cells), e.g., to promote the formation of new tissue after implantation. Thus, for example, growth factors, cytokines, extracellular matrix components, and other bioactive materials can be added to the substrate to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

The biocompatible substrate may be shaped using methods such as, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, the substrate is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the tissue. Next a solvent is used to dissolve away one of the components, resulting in pore formation. (See Mikos, U.S. Pat. No. 5,514,378, hereby incorporated by reference).

In nucleation, thin films in the shape of the tissue are exposed to radioactive fission products that create tracks of radiation damaged material. Next, the polycarbonate sheets are etched with acid or base, turning the tracks of radiation-damaged material into pores. Finally, a laser may be used to shape and burn individual holes through many materials to form a tissue structure with uniform pore sizes. The substrate can be fabricated to have a controlled pore structure that allows nutrients from the culture medium to reach the deposited cell population. In vitro cell attachment and cell viability can be assessed using scanning electron microscopy, histology and quantitative assessment with radioisotopes.

Thus, the substrate can be shaped into any number of desirable configurations to satisfy any number of overall system, geometry or space restrictions. The matrix can be shaped to different sizes to conform to the necessary structures of different sized patients.

A substrate can also be permeated with a material, for example liquified copolymers (poly-DL-lactide co-glycolide 50:50 80 mg/ml methylene chloride) to alter its mechanical properties. This can be performed by coating one layer, or multiple layers until the desired mechanical properties are achieved.

The substrate can also be treated or seeded with various factors and proteins to control the degradation/absorption of the matrix in the subject. For instance, if the cells seeded within the substrate are slow-growing, then it is beneficial to maintain the matrix integrity for a long enough period of time to allow the cells enough time to regenerate and grow. On the other hand, if the cells are able to quickly reproduce and grow, then a short lived substrate could be desirable. Varying the concentration of aprotinin additives, aminocaproic acid, tranxemic acid, or similar fibrinolytic inhibitors or the degree of chemical cross-linking in the matrix could be used to precisely control this variable. The substrate could also be seeded with varying growth factors such as angiogenesis factor to promote a growth of blood vessels upon implantation.

V. In Vivo Self-Seeding Matrix

Figure 3:
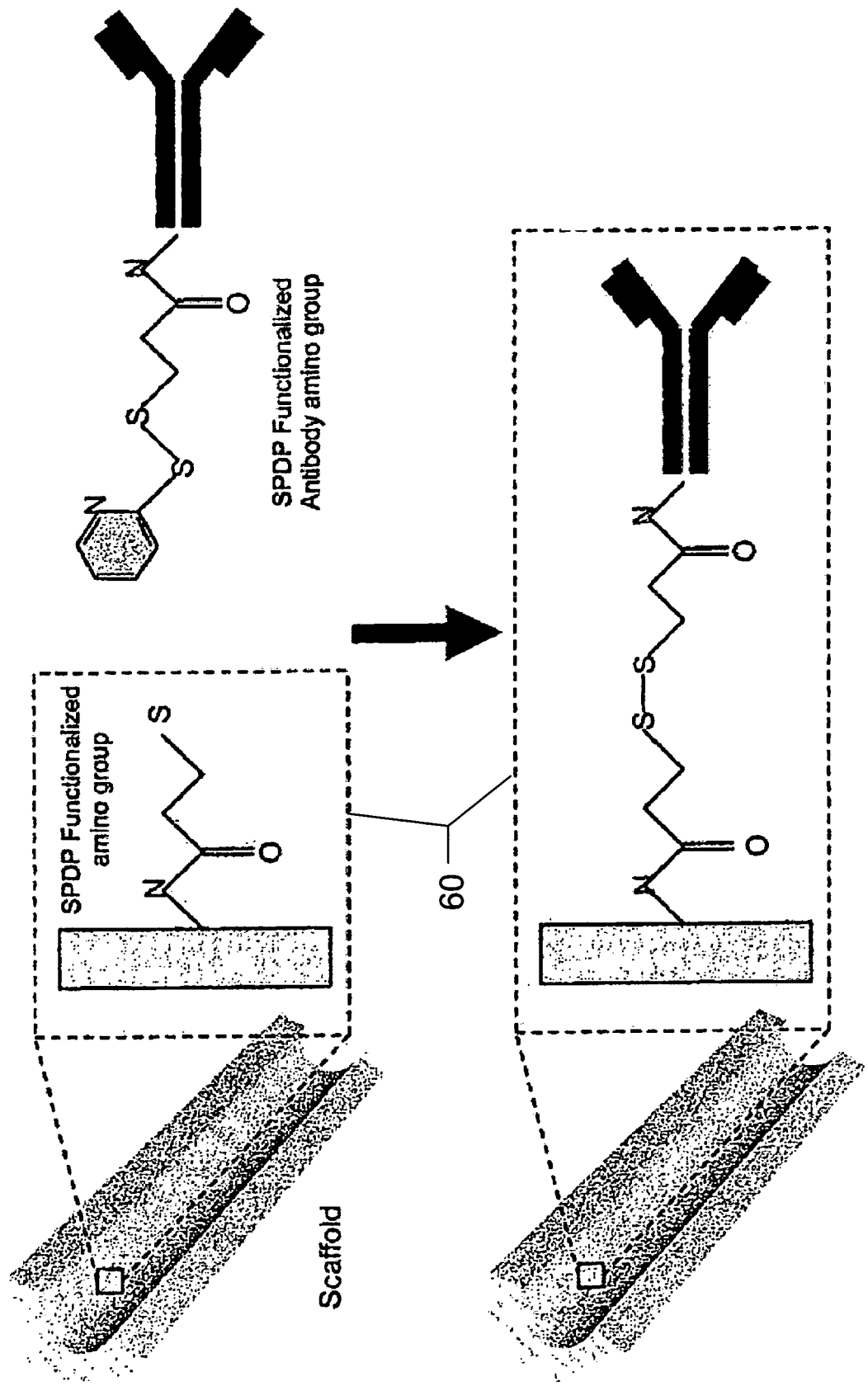
FIG. 3 is a schematic diagram showing the generation of self seeding vascular graft using SPDP or other functionalizing agents, 60, to create a covalent bond with an antibody or antibody fragment.

In another aspect, the inventions provides a self-seeding scaffold for in vivo seeding of target cells comprising a biomatrix covalently coupled to an affinity moiety with substantial specificity for binding to a target cell population, wherein the affinity moiety is capable of attacting and binding to said target cells. The biomatrix can be, for example, a synthetic matrix or a decellularized matrix. The biomatrix can be a stent or prosthetic. In some embodiments, the biomatrix is covalently coupled to the affinity moiety using a linker. The invention also provides a method of in vivo biomaterial seeding. For example, one or more affinity moieties directed a target cell type (e.g. stem cells) can be covalently attached (such as by the crosslinking agent SPDP (N-succinimidyi-3-(2-pyridyldithio)propionate, 1-Ethyl-3-[3-dimethylaminopropyl]carbodiimide hydrochloride (EDC or EDAC), N-hydroxysulfosuccinimide (Sulfo-NHS), or N-hydroxysuccinimide (NHS),) to a biomatrix to attract the target cells to vessels/organs in vivo (FIG. 3). This feature would attract the target cells to the biomatrix, precluding the need for in-vitro culture of these cells and allow their development in a more conducive in vivo environment. In preferred embodiments, NHS is used for the covalent cross-linking to the beads, whereas EDC and SPDP is used for the scaffold covalent bonding of antibody to the graft.

In another embodiment to the invention, the self-seeding scaffold can comprise a recombinant protein comprising the affinity moiety is genetically attached to the matrix. The recombinant protein can be a single chain antibody, protein, or peptide genetically engineered to also comprise a matrix molecule, such as collagen, for instance, to create a chimeric protein. The recombinant protein and/or chimeric protein can also be woven or incorporated into the matrix and can be exposed from the matrix to display the affinity moiety capable of binding to circulating cells.

Once seeded onto the matrix, the cells will proliferate and develop on the matrix to form a tissue layer. Importantly, because the matrix has an infra-structure that permits culture medium to reach the tissue layer, the cell population continues to grow, divide, and remain functionally active to develop into a tissue that has a morphology which resembles the analogous structure in vivo.

It is important to recreate, in culture, the cellular microenvironment found in vivo for the particular tissue being engineered. By using a matrix that retains an infra-structure that is similar or the same as an in vivo tissue structure, the optimum environment for cell-cell interactions, development and differentiation of cell populations, is created.

In one aspect of the present invention, cells can be seeded directed onto the biomatrix implanted in a subject, therefore eliminating the need to culture the cells in vitro.

Growth factors and regulatory factors can be added to the media to enhance, alter or modulate proliferation and cell maturation and differentiation in the cultures. The growth and activity of cells in culture can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

The artificial tissue constructs of the invention can be used in a variety of applications. For example, the artificial tissue constructs can be implanted into a subject to replace or augment existing tissue. The subject can be monitored after implantation of the artificial tissue or organ, for amelioration of the disorder.

The artificial tissue can be used in vitro to screen a wide variety of compounds, for effectiveness and cytotoxicity of pharmaceutical agents, chemical agents, growth/regulatory factors. The cultures can be maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the artificial tissue may be assessed.

Other embodiments and used of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the claims.

EXAMPLES

Example 1

Methods and Materials

Animals:

Young female sheep between the ages of 4 and 12 months were purchased from RSI Farms (Mocksville, N.C.). All procedures were approved by the Wake Forest Animal Care and Use Committee. Sheep were monitored peri-operatively for any evidence of neurologic, cardiovascular, allergic, or pulmonary complications. Physiologic parameters included heart rate, blood pressure, end tidal carbon dioxide and pulse oximetry before, during and immediately following cycling of the ECA column or sham operated animals. Hematological monitoring included complete blood counts (CBC) with differential drawn immediately prior to column cycling and 24 hours post-operatively (n=8). In control animals blood work was performed immediately following vascular exposure and twenty four hours post-operatively.

Antibodies:

Anti-CD133 IgG1 monoclonal antibody was prepared from the AC133.1 hybridoma line (ATCC, Manassas, Va.) by in vitro antibody production using a gas permeable culture system (UNC Immunology Core, Chapel Hill, N.C.). Antibody was then purified by Hi-Trap Protein G cartridges (GE Healthcare, Piscataway, N.J.). Mouse isotype control IgG1 (MOPC-21) was purchased from Sigma (St. Louis, Mo.). Both antibodies were concentrated and dialyzed into phosphate buffered saline pH 7.4 using Ultra-15 centrifugal 50 kDa concentrating devices (Millipore, Billerica, Mass.) according to manufacturer's directions.

Antibody Conjugation of NHS Sepharose Beads:

CD133 or isotype control antibodies (5 mg/mL) were conjugated at a ratio of 500 μg/mL of NHS Fastflow sepharose (GE Healthcare) according to manufacturer's instructions. Bead sizes ranged between 45-165 μm. To remove beads which would not be retained by 70 μm pore size column mesh dividers, sepharose was first rinsed over a 70 μm nylon mesh cell strainer (BD Biosciences, San Jose, Calif.). Beads were stored in 0.1% sodium azide saline and washed overnight in sterile azide-free saline twice before use.

Extracorporeal Cellular Affinity (ECA) Column

Columns were created using 50 mL Falcon tubes (BD Biosciences, San Jose, Calif.) and three 70 μm filter mesh strainers (BD Biosciences), gas sterilized with ethylene oxide gas were and then assembled with 1 milliliter of conjugated beads evenly distributed amongst the three mesh filters of the column. Preoperatively, animals received a single dose of clopidogrel 75 mg and aspirin 375 mg orally the day prior to surgery. After two days of fasting, sheep were placed under isoflurane general anesthesia followed by vascular exposure of the carotid or superficial femoral artery and the jugular or superficial femoral vein, respectively, and the vessels were cannulated with the taper cut end of sterile arterial monitoring tubing (Arrow International, Reading, Pa.). The circuit was completed by connecting tubing to each end of the column and blood was cycled for a volume of 1800 mL. Flow rates were established during each column cycling by means of a three way stopcock in the circuit allowed timed collection of blood beyond the column and this value was then used to calculate the cycle times required to attain the 1800 volume. Columns were then rinsed with sterile saline and placed on ice until cell recovery. Vessels were then decannulated and repaired with 6-0 polypropylene suture (Surgipro, Syneture, Norwalk, Conn.).

Cell Recovery:

After cycling the ECA column, beads were removed from each column and rinsed with sterile saline over 70 μm mesh filters to remove unbound cells. Beads were then treated with 0.05% trypsin-EDTA (Gibco, Grand Island, N.Y.) for 10 minutes at 37 degrees and separated from beads by rinsing through a new mesh strainer. Cells were then pelleted by centrifuge and resuspended in EGM2 endothelial growth media (Cambrex, East Rutherford, N.J.) for endothelial culture or subsequent receptor analysis. Buffy coat leukocyte were prepared from freshly heparinized peripheral blood specimens as previously described using gradient centrifugation with Histopaque 1077 (Sigma, St. Louis, Mo.) (Kaushal, S., et al., *Functional small-diameter neovessels created using endothelial progenitor cells expanded ex vivo*. Nat Med, 2001. 7(9): p. 1035-40.)

Assessment of CD133 Expression:

ECA column derived cells or buffy coat leukocytes were incubated in EGM2 media for 6 hours prior to analysis to allow for recovery of cell surface receptor expression. Equivalent numbers of buffy coat derived leukocytes or column derived cells were incubated with the biotinylated anti-CD133 antibody 293 (Miltenyi, Auburn, Calif.) for 40 minutes. Cells were then rinsed in PBS and stained with FITC avidin (Vector Laboratories, Burlingame, Calif.) according to manufacturer's instructions. After being cytospun onto glass slides, cells were mounted with DAPI-containing mouting media (Vector) and examined under fluorescent microscopy with dual color imaging.

Endothelial Progenitor Colony Forming Unit Assay:

Cells recovered from 1800 mL of blood using either CD133 ECA or isotype IgG control ECA columns were plated into fibronectin coated 24 well plates (Costar, Lowell, Mass.), at a density of 25,000 cells per well in EGM2 media. The entire eluted cell population was plated in this manner. As a control, buffy coat leukocytes collected from the same animal prior to column cycling were plated at the same density into a matching number of 24 well plates such that the same number of wells were plated for both the ECA column and buffy leukocyte cells. As very few cells were recovered by the IgG isotype control ECA column than the CD133 ECA column, fewer wells were necessarily plated. Media was changed at 5 and 8 days after the initial plating, then at day 9 colonies in each well were counted by a blinded observer experienced with endothelial colony morphology. Colony counts were then expressed as the yield from each column (CD133 or isotype control, n=4 for each) and for the matching number of buffy leukocyte plated wells (n=8, four matching sets for each of the two column conditions). In a separate buffy leukocyte colony assay, buffy coat leukocytes purified from 10 milliliters of freshly heparinized blood specimen were plated at 10 mL worth of cells per well of a fibronectin coated 6 well dish in EGM2 media. Nonadherent cells were serially passaged to new fibronectin coated plates every 24 hours over 3 days. Colonies were then counted as described under the endothelial progenitor colony forming unit assay. Of note, no colonies were noted prior to 7 days on either buffy leukocyte or ECA purified cells. Immunohistochemistry: Cells were plated onto FBN coated glass chamber slides (Nunc, Rochester, N.Y.) in EGM2 media. When cells reached 90% confluence these wells were fixed with formalin, rinsed in PBS, then blocked with staining buffer containing 2% FBS and 0.2% Triton-X in PBS. Chambers were then incubated with antibodies directed towards vWF (DAKO, Carpinteria, Calif.) and eNOS (#610297, Transduction Laboratories, San Jose, Calif.) using 1:25 and 1:50 dilutions. For staining of Lectin, cells were incubated with biotinylated UEA Lectin (Vector). Primary antibodies or lectin were then localized with FITC anti-rabbit, FITC anti-Mouse, or FITC avidin (Vector) at 1:100 dilution.

Growth Curves:

The entirety of endothelial colonies derived from a single 1800 mL cycle of the CD133 ECA column (n=4) were expanded at between ten to eleven days post initial plating when cells had become over 90% confluent. Because of a low expected frequency of colony appearance in buffy leukocyte group (colony outgrowth in only 44% of wells) colonies were assessed from larger number of specimens (n=18). Buffy leukocyte derived colonies were passaged for the first time when the colony or colonies became 2 mm in size. To normalize cell plating density at each passage, trypsinized endothelial cells from either source were seeded at 10,000 cells per square cm in as many culture dishes required to accommodate all cells at this density. Cells were progressively passaged until reaching ten million cells as assessed by hemocytometer counts of trypsin released cells. Ten million cells was chosen as this is the cell number routinely used to seed bioengineered vascular grafts in our laboratory.

Statistics:

Intraoperative physiologic data and changes in cell counts (pre-versus post-operative) were compared between column and control animals with Wilcoxon rank sum testing using exact methods. Endothelial cell growth curves for column-isolated versus buffy leukocyte-derived cultures were compared using survival analysis, with the survival endpoint defined as number of days to reach >=10 million cells. Data for the growth curve analysis are expressed as a median time to achieve this target cell number with confidence intervals as shown.

Example 2

Hematologic and Physiologic Stability During Column Use

The ECA columns consists of sepharose matrix with antibody based affinity towards the progenitor antigen CD133 retained by mesh filters (FIG. 1A). The extracorporeal circuit consists of an arterial cannula carrying blood to the column and the blood is then returned to the donor by a venous cannula to complete the circuit in anesthetized sheep after femoral or carotid vascular exposure. Given the expected turbulent environment of a device cycling high volumes of blood and the theoretical potential for allergic reaction or disturbed hematologic parameters, perioperative hematologic and physiologic parameters were assessed in sham operated control and column cycled animals. Complete blood counts with differential were assessed before and after cycling of the ECA column as well as in control animals. A comparison CBC, drawn 24 hours after the surgery, revealed a postoperative elevation of neutrophils and eosinophils that was small but statistically significant from control animals. No significant depletion of platelets, neutropenia and no significant decrements in hematocrit of column cycled were observed relative to control animals (Table 1). From a physiologic standpoint, sheep vitals including heart rate, blood pressure, end tidal carbon dioxide and pulse oximetry were not significantly different between column cycled versus sham operated control animals ($p > 0.05$ for all variables) (Table 2).

TABLE 1

| Physiologic Parameter | Sham Control Mean (n = 8) | ECA Column Mean (n = 8) | p-value |
| --- | --- | --- | --- |
| Heart Rate | 95.74 | 104.63 | 0.489 |
| Systolic BP | 98.02 | 106.62 | 0.982 |
| Diastolic BP | 64.34 | 70.92 | 1.000 |
| End-Tidal CO2 | 88.70 | 93.90 | 1.000 |
| O2 Saturations | 45.41 | 42.65 | 0.863 |

TABLE 2

| Cell Type | Sham Control (n = 8) | | | ECA Column (n = 8) | | | p-value |
| --- | --- | --- | --- | --- | --- | --- | --- |
| | Pre | Post (24 h) | Change | Pre | Post (24 h) | Change | |
| WBC | 5.25 | 6.73 | 1.48 | 5.12 | 8.15 | 3.03 | 0.130 |
| Neutrophil | 2.04 | 2.81 | 0.77 | 1.75 | 4.05 | 2.30 | 0.028 |

TABLE 2-continued

| Cell Type | Sham Control (n = 8) | | | ECA Column (n = 8) | | | |
|---|---|---|---|---|---|---|---|
| | Pre | Post (24 h) | Change | Pre | Post (24 h) | Change | p-value |
| Eosinophil | 0.18 | 0.19 | 0.01 | 0.16 | 0.37 | 0.21 | 0.065 |
| Hematocrit | 31.56 | 33.31 | 1.75 | 33.43 | 44.14 | 10.71 | 0.010 |
| Platelets | 443.13 | 355.38 | −87.75 | 496.75 | 526.38 | 29.63 | 0.161 |

Example 3

Characterization of Cells Recovered by the ECA Column

Figure 4A:
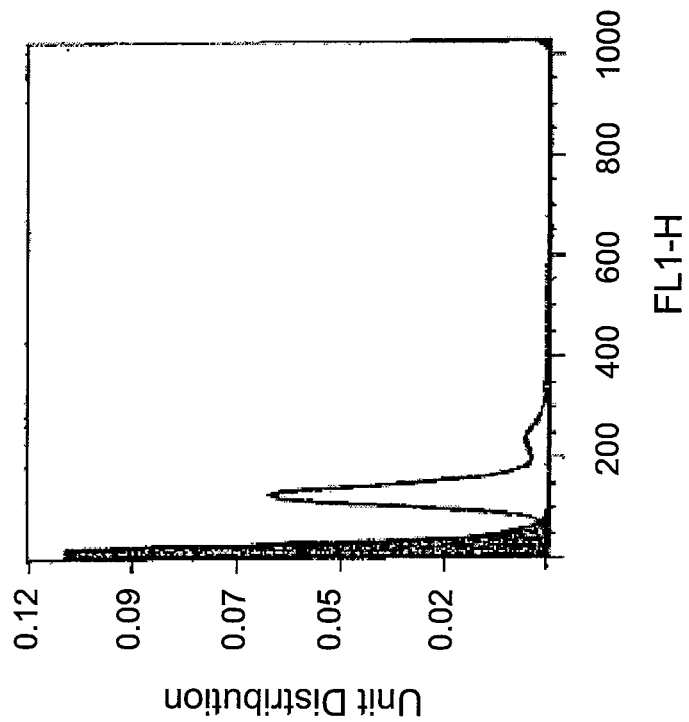
FIGS. 4A & B are graphs showing that relative to the entire leukocyte population of peripheral blood (shaded curve), cells extracted by the CD133 purification cartridge (solid line) demonstrate substantially higher expression of (A) CD133 and (B) CD34.
Figure 4B:
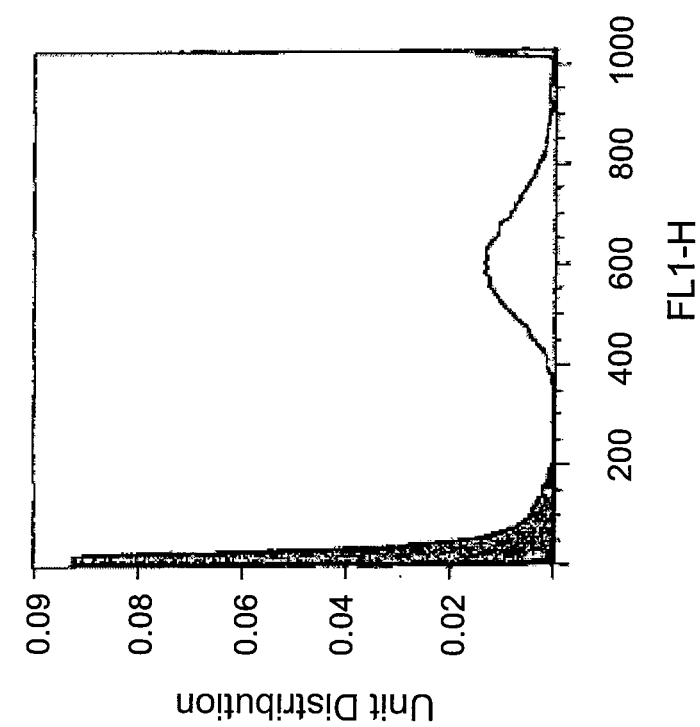

To demonstrate enrichment of CD133 positive cells recovered by the column, eluted cells were compared to buffy leukocytes for expression of the marker CD133 by fluorescent immunohistochemistry. Cells were cultured for 8 hours to allow for recovery of receptor expression and stained by FITC labeled anti-CD133 antibody and counterstained with DAPI. Comparable cell densities were stained with the DAPI nuclear counterstain and while buffy coat derived cells exhibited only a rare positive staining cell, ECA column recovered cells demonstrated a predominance of CD133 positive cells. In addition, relative to the entire leukocyte population of peripheral blood (shaded curve), cells extracted by the CD133 purification cartridge (solid line) demonstrated substantially higher expression of CD133 (FIG. 4A) and CD34 (FIG. 4B).

Example 4

Increased Endothelial Colony Forming Units from Column Purified Cells

Figure 5:
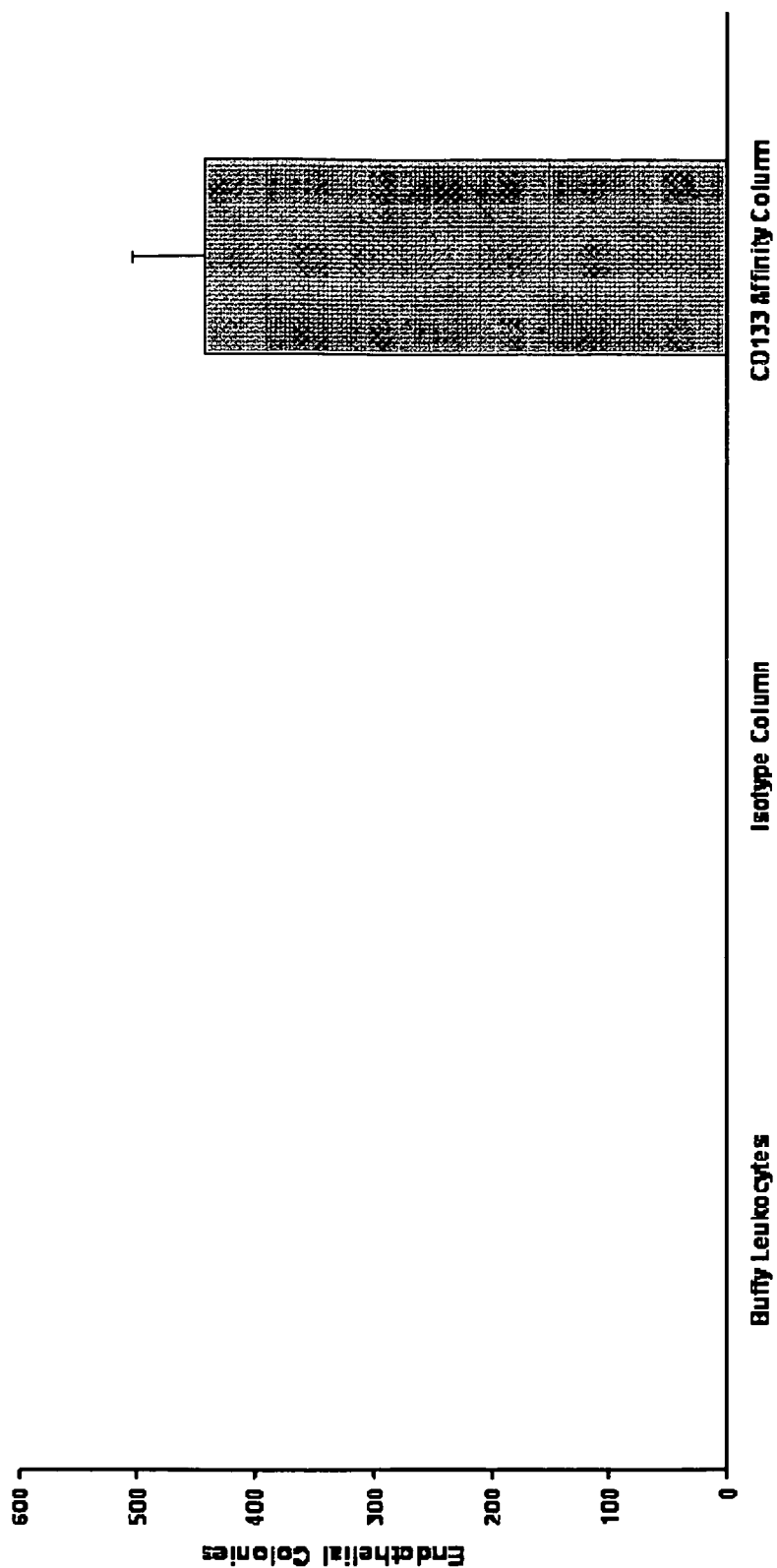
FIG. 5 is a bar graph comparing endothelial colony outgrowth of column eluted cells versus controls. Cells recovered after cycling 1800 mL of blood through the CD133 ECA column were plated on fibronectin coated 24-well plates at twenty-five thousand cells per well. An equivalent density of buffy coat leukocytes and cells recovered from an IgG isotype ECA column and observed for endothelial colony outgrowths (n=4 for each of column groups and n=8 for buffy leukocyte cells).

An important question with regards to column purified CD133 positive cells is whether this would necessarily translate to an increased number of colony forming units when compared to either a IgG isotype control ECA column or buffy leukocytes plated at a similar density with an equivalent number of cells. Twenty five thousand cells eluted from CD133 or mouse isotype IgG control ECA columns, were compared to buffy coat leukocytes from the same animal. Cells were plated under identical conditions and assessed for colony forming units at 9 days. Cells recovered from a CD133 ECA column generated an average of 444 colonies per column, while no colonies were generated from either the mouse isotype control recovered cells or buffy leukocytes (FIG. 5). To define the volume of blood from which buffy leukocytes would generate an endothelial colony, a separate assay with a larger number of cells was conducted using the equivalent of 10 mL worth of buffy derived leukocytes. The average initial leukocyte count recovered from this volume of blood averaged at 13.5 million cells. When cultured for four weeks, the average yield was only 0.72 colonies from each 10 mL of peripheral blood (n=18). Further, only 44% of wells plated with leukocytes from this volume of blood formed any colonies. In comparison, the number of buffy leukocyte derived colonies extrapolated to 1800 mL would be 130 while the number of colonies actually recovered by the ECA column for this volume of blood was over three times as high at 444 colonies. When compared to a 10 mL blood specimen processed as buffy coat leukocytes, a single run of the ECA column generates over 600 fold more endothelial colonies.

Example 5

Characterization of Column Derived Endothelial Cells

In order to establish that endothelial cells differentiated from buffy leukocyte derived progenitors were phenotypically identical to those derived from CD133 ECA purified cells, immunohistochemistry (IHC) was performed for four endothelial cell antigens. Both buffy leukocyte and ECA column derived cells were found to express endothelial markers endothelial nitric oxide synthase (eNOS), ulex lectin, vascular endothelial growth factor receptor (VEGFR), and von willebrand factor (vWf).

Example 6

Improved Growth Kinetics of Column Derived Endothelial Cells

The time advantage of this approach was evaluated in an isolated from an isolated blood specimen, 10 milliliters (mL) for instance, relative to cells from a single column cycling. To quantitatively compare the endothelial expansion of a standard ECA column run to the yield from buffy leukocytes of a 10 mL peripheral blood specimen, resultant colonies were expanded to an endpoint of 10 million cells with normalization of cell density with each passage. As illustrated in Table 3, the increased starting number of progenitor cells from the ECA column conferred an expected expansion advantage, attaining the endpoint at a lower passage nearly three times earlier (p<0.0001) than the buffy leukocyte derived endothelial cells. Further, despite maintenance at a similar cell density as their column derived counterparts, 25% of buffy derived colony sets exhausted their growth potential before attaining the 10 million cell target.

TABLE 3

| Endothelial Cell Source | Median time to 10 million cells | 95% Confidence Interval |
|---|---|---|
| Buffy Leukocyte (n = 18) | 35 days | (34.0-∞) |
| ECA Column (n = 4) | 12.5 days | (12.0-14.0) |

What is claimed is:

1. A self-seeding, implantable scaffold for in vivo seeding and development of target cells comprising:
   a three-dimensional, biomatrix scaffold having a supportive framework that allows the target cells to attach and grow, wherein the biomatrix scaffold comprises a decellularized matrix having an intact acellular infrastructure comprising a collagen network with interstitial distances suitable for cell-cell interactions, the decellularized matrix being sized and shaped for implantation at a vascular or cardiac target site to augment or replace a natural biostructure that requires repair or replacement; and an affinity moiety with substantial affinity for a target stem cell population comprising endothelial progenitor cells expressing a CD133 marker, wherein the affinity moiety comprises a CD133 antibody incorporated into and covalently coupled to the decellularized matrix and is capable of attracting and binding to said CD133+ endothelial progenitor cells in vivo, following implantation at the target site, and the cells attracted by the CD133 antibody proliferate and develop on the matrix to form a laminar CD133+ endothelial progenitor cell layer.

2. The self-seeding scaffold of claim 1, wherein said affinity moiety is covalently coupled to the decellularized matrix through a crosslinking agent.

3. The self-seeding scaffold of claim 1, wherein the decellularized matrix comprises decellularized cardiac or vascular tissue.

4. The self-seeding scaffold of claim 1, wherein the decellularized matrix comprises decellularized blood vessel or heart tissue.

5. The self-seeding scaffold of claim 1, wherein the decellularized matrix is covalently coupled to the affinity moiety using a linker.

6. The self-seeding scaffold of claim 5, wherein the linker is SPDP (N-succinimidyi-3-(2-pyridyldithio)propionate).

7. The self-seeding scaffold of claim 5, wherein the linker is selected from the group consisting of (N-succinimidyi-3-(2-pyridyldithio)propionate (SPDP), 1-Ethyl-3-[3-dimethylaminopropyl]carbodiimide hydrochloride (EDC or EDAC), N-hydroxysulfosuccinimide (Sulfo-NHS), and N-hydroxysuccinimide (NHS).

8. The self-seeding scaffold of claim 1, wherein said affinity moiety is a recombinant antibody.

9. The self-seeding scaffold of claim 1, wherein the affinity moiety comprises a single chain antibody.

10. The self-seeding scaffold of claim 1, wherein the affinity moiety is a chimeric antibody comprising an antibody and a matrix molecule.

11. The self-seeding scaffold of claim 1, wherein the scaffold further comprises an affinity moiety that has substantial affinity for a CD34 marker.

12. The self-seeding scaffold of claim 1, wherein the scaffold further comprises an affinity moiety that has substantial affinity for cells selected from the group consisting of stem cells, hematopoietic stem cells, embryonic stem cells, embryonic-like stem cells, mesenchymal stem cells, myeloid stem cell, neuronal stem cells, and adult stem cells.

13. The self-seeding scaffold of claim 1, wherein the decellularized matrix is biodegradable.

14. The self-seeding scaffold of claim 1, wherein the scaffold is sized and shaped for implantation as a vascular stent.

15. The self-seeding scaffold of claim 1, wherein the scaffold is sized and shaped for implantation as a cardiac prosthesis.

* * * * *